United States Patent
Belousov

(10) Patent No.: US 9,328,384 B2
(45) Date of Patent: May 3, 2016

(54) DROPLET DIGITAL PCR WITH SHORT MINOR GROOVE PROBES

(71) Applicant: Elitech Holding B.V., Spankeren (NL)

(72) Inventor: Yevgeniy Belousov, Mill Creek, WA (US)

(73) Assignee: ELITECHGROUP B.V., Spankeren (NL)

( * ) Notice: Subject to any disclaimer, the term of this patent is extended or adjusted under 35 U.S.C. 154(b) by 0 days.

(21) Appl. No.: 14/268,133

(22) Filed: May 2, 2014

(65) Prior Publication Data

US 2014/0335515 A1  Nov. 13, 2014

Related U.S. Application Data

(60) Provisional application No. 61/822,786, filed on May 13, 2013.

(51) Int. Cl.
*C12Q 1/68* (2006.01)
*C07H 19/04* (2006.01)

(52) U.S. Cl.
CPC ............ *C12Q 1/6876* (2013.01); *C12Q 1/6818* (2013.01); *C12Q 1/6858* (2013.01)

(58) Field of Classification Search
CPC .......................... C12Q 1/6818; C12Q 1/6876
USPC ......................................... 536/26.6; 435/6.11
See application file for complete search history.

(56) References Cited

U.S. PATENT DOCUMENTS

| | | | |
|---|---|---|---|
| 6,312,894 B1 * | 11/2001 | Hedgpeth et al. | 435/6.11 |
| 6,440,706 B1 | 8/2002 | Vogelstein et al. | |
| 7,381,818 B2 | 6/2008 | Lokhov et al. | |
| 7,759,126 B2 | 7/2010 | Lokhov et al. | |
| 2009/0111100 A1 * | 4/2009 | Lukhtanov et al. | 435/6 |

FOREIGN PATENT DOCUMENTS

| | | |
|---|---|---|
| WO | 03/062445 | 7/2003 |
| WO | 2005/035545 | 4/2005 |
| WO | 2006/135765 | 12/2006 |
| WO | 2012/109500 | 8/2012 |
| WO | 2013/059725 | 4/2013 |

OTHER PUBLICATIONS

Chang, et al; Digital Single-Nucleotide Polymorphism Analysis for Allelic Imbalance; Methods Mol Med; 103: 137-141, 2005, Abstract Only.
Hindson, et al; High-Throughput Droplet Digital PCR System for Absolute Quantitation of DNA Copy Number, Analytical Chemistry; 83: 8604-8610, 2011.

(Continued)

*Primary Examiner* — Jezia Riley
(74) *Attorney, Agent, or Firm* — Jackson Walker LLP

(57) ABSTRACT

Methods for the detection of ddPCR assay-generated amplicons by short minor groove binder-fluororophore-oligonucleotide-quencher (MGB-Fl-oligo-Q) probes. The short MGB-Fl-oligo-Q probes not only reduce background, but also show improved mismatch discrimination when compared to the same length non-MGB probes for detecting the ddPCR generated targets at room temperature.

15 Claims, 5 Drawing Sheets

(56) References Cited

OTHER PUBLICATIONS

Pinheiro, et al; Evaluation of a Droplet Digital Polymerase Chain Reaction Format for DNA Copy Number Quantification; Analytical Chemistry; 84(2), 1003-1011, 2012.

Strain, et al; Highly Precise Measurement of HIV DNA by Droplet Digital PCR; PLoS One, 8(4), e55943, 1-8, Apr. 2013.

Tsui, et al; Synergy of Total PLAC4 RNA Concentration and Measurement of the RNA Single-Nucleotide Polymorphism Allelic Ratio for the Noninvasive Prenatal Detection of Trisomy 21; Clinical Chemistry, 56(1), 73-81, 2010.

Vogelstein, et al; Digital PCR; Proc. Natl. Acad. Sci. USA, 96: 9236-9241, Aug. 1999.

European Patent Office; PCT Application No. PCT/US2014/036515; International Search Report and Written Opinion; Dec. 19, 2014.

Lukhtanov, Eugeny A., et al; Novel DNA Probes With Low Background and High Hybridization-triggered Flourescence; Nucleic Acids Research, vol. 35, No. 5, Jan. 26, 2007, pp. 1-14.

The International Bureau of WIPO; PCT Application No. PCT/US2014/036515; International Preliminary Report on Patentability; Nov. 26, 2015.

* cited by examiner

SEQUENCE LISTING

<160> NUMBER OF SEQ ID NOS: 18

<210> SEQ ID NO 1
<211> LENGTH: 10
<212> TYPE: DNA
<213> ORGANISM: Artificial Sequence
<220> FEATURE:
<223> OTHER INFORMATION: 10-mer MGB probe
<220> FEATURE:
<221> NAME/KEY: misc_feature
<222> LOCATION: (1)..(1)
<223> OTHER INFORMATION: n is T connected to AP525 and MGB
<220> FEATURE:
<221> NAME/KEY: misc_feature
<222> LOCATION: (10)..(10)
<223> OTHER INFORMATION: n is C connected to Eclipse Dark Quencher

```
<400> SEQUENCE: 1 ntatttctgn                                                                  10

<210> SEQ ID NO 2
<211> LENGTH: 10
<212> TYPE: DNA
<213> ORGANISM: Artificial Sequence
<220> FEATURE:
<223> OTHER INFORMATION: 10-mer MGB probe
<220> FEATURE:
<221> NAME/KEY: misc_feature
<222> LOCATION: (1)..(1)
<223> OTHER INFORMATION: n is T connected to FAM and MGB
<220> FEATURE:
<221> NAME/KEY: misc_feature
<222> LOCATION: (5)..(5)
<223> OTHER INFORMATION: n is Super T
<220> FEATURE:
<221> NAME/KEY: misc_feature
<222> LOCATION: (10)..(10)
<223> OTHER INFORMATION: n is C connected to Eclipse dark quencher
<220> FEATURE:
<221> NAME/KEY: misc_feature
<222> LOCATION: (10)..(10)
<223> OTHER INFORMATION: n is C connected to Eclipse Dark Quencher

<400> SEQUENCE: 2 ntatntatgn                                                                  10

<210> SEQ ID NO 3
<211> LENGTH: 10
<212> TYPE: DNA
<213> ORGANISM: Artificial Sequence
<220> FEATURE:
<223> OTHER INFORMATION: 10-mer No-MGB probe
<220> FEATURE:
<221> NAME/KEY: misc_feature
<222> LOCATION: (1)..(1)
<223> OTHER INFORMATION: n is T connected to AP525
<220> FEATURE:
<221> NAME/KEY: misc_feature
<222> LOCATION: (10)..(10)
<223> OTHER INFORMATION: n is C connected to Eclipse Dark Quencher

<400> SEQUENCE: 3 ntatttctgn                                                                  10

<210> SEQ ID NO 4
<211> LENGTH: 10
<212> TYPE: DNA
<213> ORGANISM: Artificial Sequence
<220> FEATURE:
<223> OTHER INFORMATION: 10-mer No-MGB probe
<220> FEATURE:
<221> NAME/KEY: misc_feature
<222> LOCATION: (1)..(1)
<223> OTHER INFORMATION: n is T connected to FAM
<220> FEATURE:
<221> NAME/KEY: misc_feature
<222> LOCATION: (5)..(5)
<223> OTHER INFORMATION: n is Super T
<220> FEATURE:
<221> NAME/KEY: misc_feature
<222> LOCATION: (10)..(10)
<223> OTHER INFORMATION: n is C connected to Eclipse Dark Quencher

<400> SEQUENCE: 4 ntatntatgn                                                                  10
```

-continued

```
<210> SEQ ID NO 5
<211> LENGTH: 25
<212> TYPE: DNA
<213> ORGANISM: Artificial Sequence
<220> FEATURE:
<223> OTHER INFORMATION: Allele G synthetic target

<400> SEQUENCE: 5
ctgcaaatag cagaaataaa agaaa                                              25

<210> SEQ ID NO 6
<211> LENGTH: 25
<212> TYPE: DNA
<213> ORGANISM: Artificial Sequence
<220> FEATURE:
<223> OTHER INFORMATION: Allele T synthetic target

<400> SEQUENCE: 6
ctgcaaatag cataaataaa agaaa                                              25

<210> SEQ ID NO 7
<211> LENGTH: 11
<212> TYPE: DNA
<213> ORGANISM: Artificial Sequence
<220> FEATURE:
<223> OTHER INFORMATION: 11-mer MGB probe
<220> FEATURE:
<221> NAME/KEY: misc_feature
<222> LOCATION: (1)..(1)
<223> OTHER INFORMATION: n is T connected to AP525 and MGB
<220> FEATURE:
<221> NAME/KEY: misc_feature
<222> LOCATION: (11)..(11)
<223> OTHER INFORMATION: n is C connected to Eclipse Dark Quencher

<400> SEQUENCE: 7
ntatttctgc n                                                             11

<210> SEQ ID NO 8
<211> LENGTH: 11
<212> TYPE: DNA
<213> ORGANISM: Artificial Sequence
<220> FEATURE:
<223> OTHER INFORMATION: 11-mer MGB probe
<220> FEATURE:
<221> NAME/KEY: misc_feature
<222> LOCATION: (1)..(1)
<223> OTHER INFORMATION: n is T connected to FAM and MGB
<220> FEATURE:
<221> NAME/KEY: misc_feature
<222> LOCATION: (5)..(5)
<223> OTHER INFORMATION: n is Super T
<220> FEATURE:
<221> NAME/KEY: misc_feature
<222> LOCATION: (11)..(11)
<223> OTHER INFORMATION: n is Super T connected to Eclipse Dark Quencher

<400> SEQUENCE: 8
ntatntatgc n                                                             11

<210> SEQ ID NO 9
<211> LENGTH: 16
<212> TYPE: DNA
<213> ORGANISM: Artificial Sequence
<220> FEATURE:
<223> OTHER INFORMATION: 16-mer MGB probe
<220> FEATURE:
<221> NAME/KEY: misc_feature
<222> LOCATION: (1)..(1)
<223> OTHER INFORMATION: n is T connected to AP525 and MGB
```

```
<220> FEATURE:
<221> NAME/KEY: misc_feature
<222> LOCATION: (16)..(16)
<223> OTHER INFORMATION: n is G connected to Eclipse Dark Quencher

<400> SEQUENCE: 9
ntatttctgc tatttn                                                      16

<210> SEQ ID NO 10
<211> LENGTH: 17
<212> TYPE: DNA
<213> ORGANISM: Artificial Sequence
<220> FEATURE:
<223> OTHER INFORMATION: 17-mer MGB probe
<220> FEATURE:
<221> NAME/KEY: misc_feature
<222> LOCATION: (1)..(1)
<223> OTHER INFORMATION: n is T connected to FAM and MGB
<220> FEATURE:
<221> NAME/KEY: misc_feature
<222> LOCATION: (6)..(6)
<223> OTHER INFORMATION: n is Super T
<220> FEATURE:
<221> NAME/KEY: misc_feature
<222> LOCATION: (15)..(15)
<223> OTHER INFORMATION: n is Super T
<220> FEATURE:
<221> NAME/KEY: misc_feature
<222> LOCATION: (16)..(16)
<223> OTHER INFORMATION: n is Super T
<220> FEATURE:
<221> NAME/KEY: misc_feature
<222> LOCATION: (17)..(17)
<223> OTHER INFORMATION: n is G connected to Eclipse Dark Quencher

<400> SEQUENCE: 10
nttatntatg ctatnnn                                                     17

<210> SEQ ID NO 11
<211> LENGTH: 30
<212> TYPE: DNA
<213> ORGANISM: Artificial Sequence
<220> FEATURE:
<223> OTHER INFORMATION: 30-mer dual labeled probe
<220> FEATURE:
<221> NAME/KEY: misc_feature
<222> LOCATION: (1)..(1)
<223> OTHER INFORMATION: n is A connected to Hex
<220> FEATURE:
<221> NAME/KEY: misc_feature
<222> LOCATION: (30)..(30)
<223> OTHER INFORMATION: n is G connected to Eclipse Dark Quencher

<400> SEQUENCE: 11
nccctgcaaa tagcagaaat aaaagaaaan                                       30

<210> SEQ ID NO 12
<211> LENGTH: 30
<212> TYPE: DNA
<213> ORGANISM: Artificial Sequence
<220> FEATURE:
<223> OTHER INFORMATION: 30-mer dual labeled probe
<220> FEATURE:
<221> NAME/KEY: misc_feature
<222> LOCATION: (1)..(1)
<223> OTHER INFORMATION: n is A connected to FAM
<220> FEATURE:
<221> NAME/KEY: misc_feature
<222> LOCATION: (30)..(30)
<223> OTHER INFORMATION: n is G connected to Eclipse Dark Quencher
```

```
<400> SEQUENCE: 12
nccctgcaaa tagcataaat aaaagaaaan                              30

<210> SEQ ID NO 13
<211> LENGTH: 28
<212> TYPE: DNA
<213> ORGANISM: Artificial Sequence
<220> FEATURE:
<223> OTHER INFORMATION: Forward primer

<400> SEQUENCE: 13
gacacaggaa gcagattctg ctaatacc                                28

<210> SEQ ID NO 14
<211> LENGTH: 26
<212> TYPE: DNA
<213> ORGANISM: Artificial Sequence
<220> FEATURE:
<223> OTHER INFORMATION: Reverse primer

<400> SEQUENCE: 14
cacaggatct tcagctgacc tagttc                                  26

<210> SEQ ID NO 15
<211> LENGTH: 10
<212> TYPE: DNA
<213> ORGANISM: Artificial Sequence
<220> FEATURE:
<223> OTHER INFORMATION: 10-mer MGB probe
<220> FEATURE:
<221> NAME/KEY: misc_feature
<222> LOCATION: (1)..(1)
<223> OTHER INFORMATION: n is Super G connected to AP525 and MGB
<220> FEATURE:
<221> NAME/KEY: misc_feature
<222> LOCATION: (10)..(10)
<223> OTHER INFORMATION: n is G connected to Eclipse Dark Quencher

<400> SEQUENCE: 15 nagctggtgn                                                    10

<210> SEQ ID NO 16
<211> LENGTH: 10
<212> TYPE: DNA
<213> ORGANISM: Artificial Sequence
<220> FEATURE:
<223> OTHER INFORMATION: 10-mer MGB probe
<220> FEATURE:
<221> NAME/KEY: misc_feature
<222> LOCATION: (1)..(1)
<223> OTHER INFORMATION: n is Super G connected to FAM and MGB
<220> FEATURE:
<221> NAME/KEY: misc_feature
<222> LOCATION: (10)..(10)
<223> OTHER INFORMATION: n is G connected to Eclipse Dark Quencher

<400> SEQUENCE: 16 nagctgatgn                                                    10

<210> SEQ ID NO 17
<211> LENGTH: 30
<212> TYPE: DNA
<213> ORGANISM: Artificial Sequence
<220> FEATURE:
<223> OTHER INFORMATION: Forward primer

<400> SEQUENCE: 17
cctgctgaaa atgactgaat ataaacttgt                              30
```

```
<210> SEQ ID NO 18
<211> LENGTH: 20
<212> TYPE: DNA
<213> ORGANISM: Artificial Sequence
<220> FEATURE:
<223> OTHER INFORMATION: Reverse primer

<400> SEQUENCE: 18
gctgtatcgt caaggcactc                                            20
```

DROPLET DIGITAL PCR WITH SHORT MINOR GROOVE PROBES

This application claims priority to U.S. Provisional Patent Application Ser. No. 61/822,786, filed May 13, 2013, entitled "Droplet Digital PCR with Short Minor Groove Probes," the entire content of which is hereby incorporated by reference.

FIELD OF THE INVENTION

The present invention relates to droplet digital polymerase chain reaction (PCR) techniques, and more specifically to the detection of ddPCR assay-generated amplicons by short minor groove binder-fluororophore-oligonucleotide-quencher (MGB-Fl-oligo-Q) probes.

BACKGROUND

In real-time PCR, quantitative information is obtained from the cycle threshold (Co), a point where the fluorescence curve signal increases above background. External calibrators are required to estimate the concentration of unknown samples. The variation in amplification efficiency affects Cq values which in turn limits the accuracy of techniques for absolute quantitation. It is recognized that the combination of limiting dilution, end-point PCR, and Poisson statistics can determine the absolute measure of nucleic acid concentration (Vogelstein and Kinzler, U.S. Pat. No. 6,440,706).

Digital single-nucleotide polymorphism (SNP) analysis has been developed to amplify a single template from a pool of DNA samples, thereby generating amplicons that are homogeneous in sequence. Different fluorescently-labeled probes are used to detect and discriminate different alleles (e.g. paternal vs. maternal alleles or wild-type vs. mutant alleles), which can be readily counted. The advantages of digital PCR have been reported (Chang and Shih). Currently there are basically two commercially available digital PCR systems. The first one uses microfluidic chambers or microwells to split samples into aliquots on the order of hundreds of nanoliters. The second system involves emulsion PCR, wherein templates are clonally amplified in the presence of beads which are recovered from the emulsion, then hybridized with a hybridization probe and read by conventional flow-cytometry. These approaches are ideally suited for single-nucleotide polymorphism analysis and for allelic imbalance detection (Hindson, Tsui; the content of which is incorporated herein by reference). Different probes have been used for the detection of digital PCR-generated amplicons, for example, molecular beacons (U.S. Pat. No. 6,440,706) and MGB TaqMan and dual-labeled non-MGB TaqMan probes (Hindson). Typically, these probes are longer than 16 bases. The TaqMan probes are cleaved by polymerases with 5'-exonuclease activity. In some applications droplet digital PCR (ddPCR) is used to make highly precise measurement of DNA, for example HIV DNA (Strain).

Digital PCR is performed to end-point (35-45 cycles) in a conventional thermocycler. Samples and oil are introduced into a droplet generator and loaded into 96-well PCR plate. Droplets from each well are placed onto a reader which moves them in single file past a two-color fluorescent detector at room temperature. Although digital PCR shows vast improvement in precision and sensitivity, longer probes tend to hybridize non-specifically.

Minor groove binder-fluororophore-oligonucleotide-quencher (MGB-Fl-oligo-Q) probes have been disclosed in U.S. Pat. Nos. 7,381,818 and 7,759,126, the content of which is incorporated by reference, but no detection of ddPCR-generated amplicons at room temperature with these short probes has been disclosed.

SUMMARY

The present invention pertains to the detection of ddPCR assay-generated amplicons by short minor groove binder-fluororophore-oligonucleotide-quencher (MGB-Fl-oligo-Q) probes.

The short MGB-Fl-oligo-Q probes function unexpectedly well as detection probes. The short MGB-Fl-oligo-Q probes not only reduce background, but also show improved mismatch discrimination when compared to the same length non-MGB probes for detecting the ddPCR generated targets at room temperature (~22° C.).

The short MGB-Fl-oligo-Q probes function unexpectedly well in allele discrimination, allowing the detection of low abundance alleles against a background of a high concentration of mutant alleles. Short minor groove binder oligonucleotide probes also allow the determination of germline copy number.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
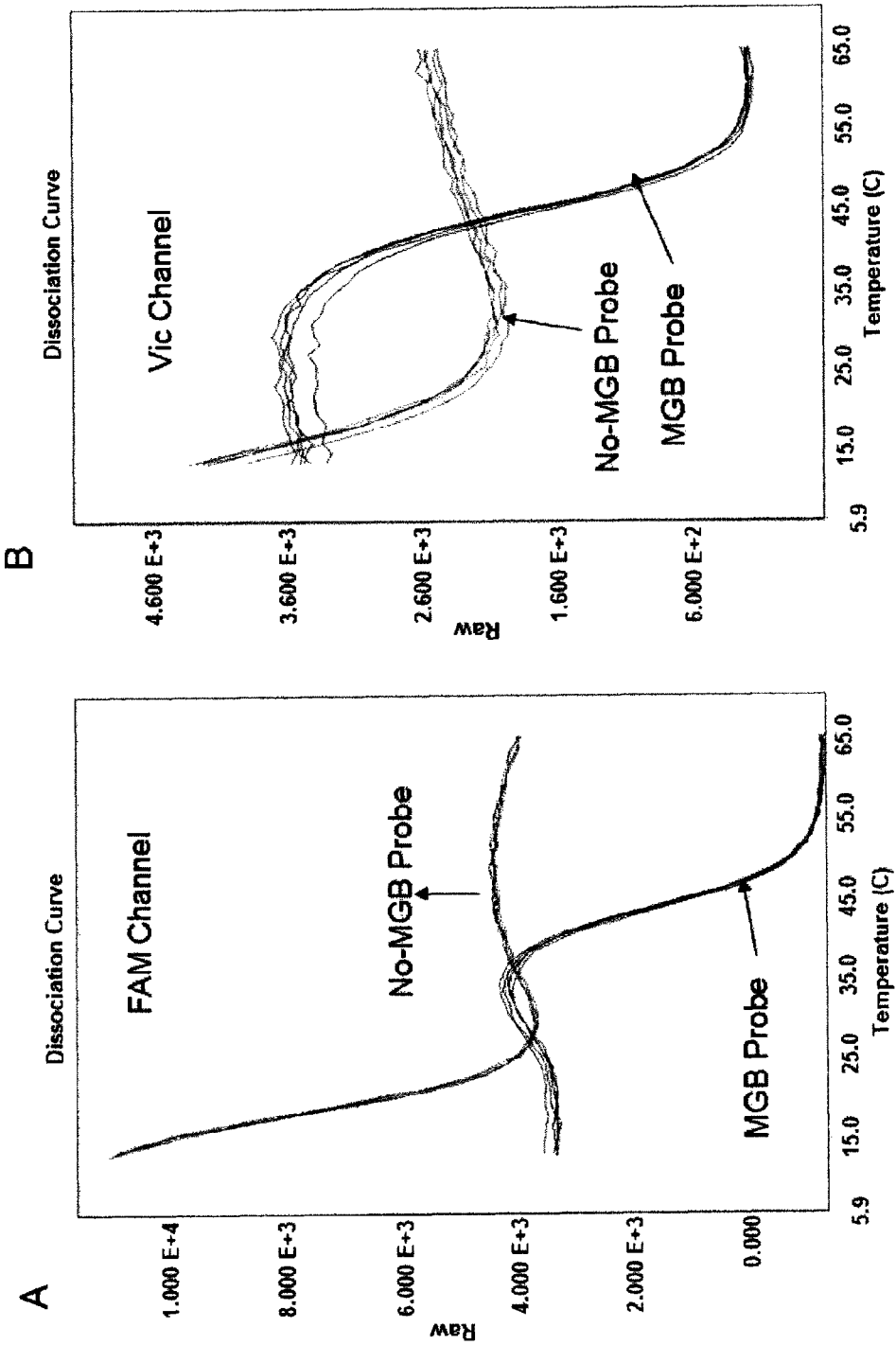
FIG. 1 shows the raw melt curves of a 10-mer MGB-Fl-oligo-Q probe and a 10-mer non-MGB probe in the FAM channel (A) and in the Vic channel (B), hybridized to a synthetic target.

The present invention relates to droplet digital polymerase chain reaction (PCR) techniques, and more specifically to the detection of ddPCR assay-generated amplicons by short minor groove binder-fluororophore-oligonucleotide-quencher (MGB-Fl-oligo-Q) probes.

I. Definitions

Unless stated otherwise, the following terms and phrases have the meanings provided below:

The term "target sequence" refers to a sequence in a target RNA, or DNA that is partially or fully complementary to the mature strand. The target sequence can be described using the four bases of DNA (A, T, G, and C), or the four bases of RNA (A, U, G, and C).

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes, including the wobble base pair formed between U and G. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. The inosine modified bases of the pending application hybridize with similar stabilities than those of normal base pairs.

The term "substantially" complementary refers to the ability of an oligonucleotide to form base pairs specifically with another oligonucleotide where said oligonucleotide may contain one or more mismatches.

The term "duplex" refers to a double stranded structure formed by two complementary or substantially complementary polynucleotides that form base pairs with one another, including Watson-Crick base pairs and U-G wobble pairs that allow for a stabilized double stranded structure between polynucleotide strands that are at least partially complementary. The strands of a duplex need not be perfectly complementary for a duplex to form, i.e., a duplex may include one or more base mismatches. In addition, duplexes can be formed between two complementary regions within a single strand (e.g., a hairpin).

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogues, as well as pyrimidines, e.g., cytosine, uracil, thymine, and their derivatives and analogues. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH2, NHR, NR2, or CN, wherein R is an alkyl moiety. Nucleotide analogues are also meant to include nucleotides with bases such as inosine, queuosine, xanthine, sugars such as 2'-methyl ribose, non-natural phosphodiester linkages such as in ethylphosphonates, phosphorothioates and peptides.

The term "modified bases" refers to those bases that differ from the naturally-occurring bases (adenine, cytosine, guanine, thymine, and urasil) by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7 deazapurines and their derivatives and pyrazolopyrimidines (described in PCT WO 01/84958); and also described in U.S. Pat. No. 6,127,121. Preferred modified bases are 5-substituted pyrimidines and 3-substituted pyrazolopyrimidines. Examples of preferred modified bases are 6-amino-1H-pyrazolo[3,4-d]pyrimidin-4(5H)-one (PPG or Super Gk), 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo pyrimidine-4-one, 6-amino-3-(3-hydroxyprop-1-yny)1-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-yny)-1,3-dihydropyrimidine-2-one, 6-amino-5-(3-aminoprop-)-yny)-1,3-dihydropyrimidine-2-one, 5-[4-amino-3-(3-methoxyprop-1-ynyl)pyrazol[3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol (Super A®), 6-Amino-3-(4-hydroxybut-1-ynyl)-1,5-dihydro-pyrazolo[3,4-d]pyrimidin-4-one, 5-(4-hydroxy-but-1-ynyl)-1H-pyrimidine-2,4-dione (Super T), 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine.

The terms "universal bases" and "degenerative bases" refer to natural base analogues that are capable of forming base pairs with two or more natural bases in DNA or RNA with little discrimination between them. Universal and degenerative bases are well known in the art and disclosed in U.S. Pat. No. 7,348,146 that is incorporated by reference. Oligonucleotide conjugates containing an inosine analog of the current disclosure may also comprise one or more universal and degenerative bases, in addition to the naturally-occurring bases adenine, cytosine, guanine, thymine and uracil.

The term "nucleotide" is also meant to include what are known in the art as universal bases. By way of example, universal bases include, but are not limited to, 3-nitropyrrole, 5-nitroindole, or nebularine. The functionalized 3-alkynyl-1H-pyrazolo[3,4-d]pyrimidin-4(5H)-ones as universal bases to A, C, T or G were disclosed in U.S. application Ser. No. 12/024,4535.

The term "nucleotide" is also meant to include the N3' to P5' phosphoramidate, resulting from the substitution of a ribosyl 3'-oxygen with an amine group. Further, the term nucleotide also includes those species that have a detectable label, such as for example a radioactive or fluorescent moiety, or mass label attached to the nucleotide.

The term "linker" refers to a moiety that is used to assemble various portions of the molecule or to covalently attach the molecule (or portions thereof) to a solid support. Additionally, a linker can include linear or acyclic portions, cyclic portions, aromatic rings or combinations thereof.

The "phosphonate or phosphonylated dyes" (e.g., dyes having a zwitterionic phosphonate group or a protected form thereof), as well as reagents incorporating those dyes (e.g., support-bound dyes and phosphoramidites) have been found to be compatible with, for example, coumarin dyes, benzocoumarin dyes, fluorescein dyes, rhodol dyes, phenoxazine dyes, benzophenoxazine dyes, xanthene dyes, benzoxanthene dyes, and cyanine dyes (U.S. Pat. Nos. 7,671,218, 7,67, 834, 8,008,522, 8,389,745 and 8,163,910 all which are incorporated herein by reference.

Examples of these and other suitable dye classes can be found in Haugland, et al., Handbook of Fluorescent Probes and Research Chemicals, Sixth Ed., Molecular Probes, Eugene, Ore. 1996; U.S. Pat. Nos. 3,194,805; 3,128,179; 5,187,288; 5,188,934; 5,227,487; 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP 1408366; Smith, et al., J. Chem. Soc. Perkin Trans. 2, 1993, 1195-1204; Whitaker, et al., Anal. Biochem. 207:267-279 (1992); Krasoviskii and Bolotin, Organic Luminescent Materials, VCH Publishers, NY., 1988; Zolliger, Color Chemistry, 2nd Edition, VCH Publishers, NY., 1991; Hirschberg, et al., Biochemistry 37:10381-10385 (1998); Fieser and Fieser, REAGENTS FOR ORGANIC SYNTHESIS, Volumes 1 to 17, Wiley, US, 1995. Geiger, et al., Nature 359:859-861 (1992). Still other dyes are provided via online sites such as http://www.zeiss.com.

There is extensive guidance in the art for selecting quencher and fluorophore pairs and their attachment to oligonucleotides (Haugland, 1996: U.S. Pat. Nos. 3,996,345 and 4,351,760 and the like). Preferred quenchers are described in U.S. Pat. No. 6,727,356, incorporated herein by reference. Other quenchers include bis azo quenchers (U.S. Pat. No. 6,790,945) and dyes from Biosearch Technologies, Inc. (provided as Black Holem Quenchers: BH-1, BH-2 and BH-3), Dabcyl, TAMRA and carboxytetramethyl rhodamine.

Minor groove binder oligonucleotide conjugates (or "probes") have been described (see U.S. Pat. Nos. 5,801,155 and 6,312,894, both incorporated herein by reference). These conjugates form hyper-stabilized duplexes with complementary DNA. In particular, sequence specificity of short minor groove binder probes is excellent for high temperature applications such as PCR. The probes/conjugates of the present disclosure can also have a covalently attached minor groove binder. A variety of suitable minor groove binders have been described in the literature. See, for example, Kutyavin, et al. U.S. Pat. No. 5,801,155; Wemmer, D. E., and Dervan. P. B., Current Opinon in Structural Biology, 7:355-361 (1997); Walker, W. L., Kopka, J. L. and Goodsell, D. S., Biopolymers, 44:323-334 (1997); Zimmer, C & Wahnert, U. Prog. Biophys. Molec. Bio. 47:31-112 (1986) and Reddy, B. S. P., Dondhi, S. M., and Lown, J. W., Pharmacol. Therap., 84:1-111 (1999).

Suitable methods for attaching minor groove binders (as well as reporter groups such as modified bases, fluorophores and quenchers) through linkers to oligonucleotides are described in, for example, U.S. Pat. Nos. RE 38,416; 5,512, 677; 5,419,966; 5,696,251; 5,585,481; 5,942,610 and 5,736, 626.

A nucleotide mono-phosphate, nucleotide di-phosphate or a nucleotide triphosphate processing enzyme is an enzyme that utilizes a nucleotide mono-phosphate, nucleotide di-phosphate or a nucleotide triphosphate as one of its substrates. A nucleotide mono-phosphate, a nucleotide di-phosphate or a nucleotide triphosphate nucleic acid processing enzyme catalyzes modifications to nucleic acids or nucleic acid intermediates using either a nucleotide mono-phosphate, nucleotide di-phosphate or a nucleotide triphosphate as one of the substrates. Nucleotide mono-phosphate, nucleotide di-phosphate or nucleotide triphosphate enzymes include but are not limited to primer extension enzymes, DNA polymerases, RNA polymerases, restriction enzymes, nicking enzymes, repair enzymes or ligation enzymes.

The synthesis of pyrazolopyrimidine-monophosphate and pyrazolopyrimidine-triphosphate analogs has been disclosed in U.S. Pat. No. RE 38,416.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, sequencing, next generation seqencing and related fields as are within the skill of the art. These techniques are fully explained in the literature. See, for example, Sambrook, Fritsch & Maniatis, Molecular Cloning: A Laboratory Manual, Second Edition, Cold Spring Harbor Laboratory Press (1989); Lee H et al., Methods Mol. Biol. 855: 155-74 (2012); Ausubel, et al., Current Protocols In Molecular Biology, John Wiley & Sons (1987, 1988, 1989, 1990, 1991, 1992, 1993, 1994, 1995, 1996); Gait (ed.). Oligonucleotide Synthesis: A Practical Approach, IRL Press (1984); Eckstein (ed.), Oligonucleotides and Analogues: A Practical Approach, IRL Press (1991).

Amplification procedures are those in which many copies of a target nucleic acid sequence are generated, usually in an exponential fashion, by sequential polymerization and/or ligation reactions. In addition to the more traditional amplification reactions discussed below, the present invention is useful in amplifications involving three-way junctures (see, WO 99/37085), signal amplification (see Capaldi, et al., Nuc. Acids Res., 28:E21 (2000)), T7 polymerases, reverse transcriptase, RNase H, RT-PCR, Rolling Circles, cleavase and the like. Isothermal amplification methods have been reviewed (cc Niemz, A. et al Trends Biotechnol., 29: 240-50 (2011)). The "term oligonucleotide primers adjacent to a probe region" refers to when 0 or one or more base separate the primer and probe. The term "overlapping with said probe region" is defined as disclosed in U.S. Pat. No. 7,319,022. The term "Ct" or "Cq" refers to the fractional PCR cycle number at which the reporter fluorescence is greater than the threshold.

Many amplification reactions, such as PCR, utilize reiterative primer-dependent polymerization reactions. A primer is a nucleic acid that is capable of hybridizing to a second, template nucleic acid and that, once hybridized, is capable of being extended by a polymerizing enzyme (in the presence of nucleotide substrates), using the second nucleic acid as a template. Polymerizing enzymes include, but are not limited to, DNA and RNA polymerases and reverse transcriptases, etc. Conditions favorable for polymerization by different polymerizing enzymes are well-known to those of skill in the art. See, for example, Sambrook et al., supra; Ausubel, et al., supra; Innis et al., supra. Generally, in order to be extendible by a polymerizing enzyme, a primer must have an unblocked 3'-end, preferably a free 3' hydroxyl group. The product of an amplification reaction is an extended primer, wherein the primer has been extended by a polymerizing enzyme.

II. Description

In one embodiment, the present invention comprises a method for discriminating mismatch in a target DNA sample, comprising contacting the target DNA sample with a minor groove binder oligonucleotide probe; and detecting a fluorescent signal from the minor groove binder oligonucleotide probe. In certain embodiments, the oligonucleotide portion of the minor groove binder oligonucleotide probe has a sequence complementary to the region of the target DNA sample in which the mismatch is located. In certain embodiments, an oligonucleotide portion of the minor groove binder oligonucleotide probe has a sequence complementary to a region of the target DNA sample, wherein the target DNA sample is digitally amplified DNA resulting from a ddPCR reaction.

The minor groove binder oligonucleotide probe of the present invention may have the formula:

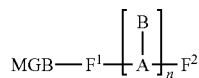

in which MGB M is a minor groove binder; $F^1$=$F^2$ is a fluorophore or a quencher with the proviso that $F^1$ and $F^2$ cannot both be quenchers or both be fluorophores; and $[A-B]_n$ represents a nucleic acid oligomer having n units, wherein n is an integer of from 9 to 11; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog or a universal or promiscuous (indiscriminative) base and the oligonucleotide portion has a sequence complementary to a portion of the target sequence being amplified in digital PCR and to provide a mixture.

In some embodiments the minor groove binder oligonucleotide probes hybridize to a digitally amplified target at room temperature, or at between about 20° C. to 25° C. or at about 22° C.

In some embodiments the minor groove binder oligonucleotide probes can be used in the determination of germline copy number.

In some embodiments the minor groove binder oligonucleotide probes can be used in the detection of a rare mutation in a large excess of wild type background.

In some embodiments, the quencher has absorption spectra between about 400 to 800 nm and the fluorophore have emission between about 400 to 800 nm.

In another embodiment, the minor groove binder oligonucleotide probe comprises at least one B independently selected from a nucleic acid base, a modified base or a base analog or a universal or promiscuous base. Preferred modified bases are Super G, Super A, Super T and Super Inosine.

In some embodiments the $F^1$ is a fluorophore and $F^2$ is a quencher and in other embodiments $F^2$ is a fluorophore and $F^1$ is a quencher. In preferred embodiments the MGB is attached at the 3'-end of the oligonucleotide.

In one embodiment, the present embodiment comprises short minor groove binders of formula:

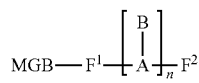

in which MGB M is a minor groove binder; $F^1$=$F^2$ is a fluorophore or a quencher with the proviso that $F^1$ and $F^2$ cannot both be quenchers or both be fluorophores; and $[A-B]_n$ represents a nucleic acid oligomer having n units, wherein n is an integer of from 9 to 11; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog or a universal or promiscuous (indiscriminative) base and the oligonucleotide portion has a sequence complementary to a portion of the target sequence being amplified in digital PCR and to provide a mixture.

In some embodiments the minor groove binder oligonucleotide probes hybridize to a digitally amplified target at room temperature.

In some embodiments the minor groove binder oligonucleotide probes can be used in the determination of germline copy number.

In some embodiments the minor groove binder oligonucleotide probes can be used in the detection of a rare mutation in a large excess of wild type background.

In some embodiments, the quencher has absorption spectra between about 400 to 800 nm and the fluorophore have emission between about 400 to 800 nm.

In another embodiment, the minor groove binder oligonucleotide probe comprises at least one B independently selected from a nucleic acid base, a modified base or a base analog or a universal or promiscuous base. Preferred modified bases are Super G, Super A, Super T and Super Inosine.

In some embodiments the $F^1$ is a fluorophore and $F^2$ is a quencher and in other embodiments $F^2$ is a fluorophore and $F^1$ is a quencher. In preferred embodiments the MOB is attached at the 3'-end of the oligonucleotide.

EXAMPLES

The following examples are provided to illustrate, but not to limit, the presently claimed invention.

PCR Amplification

PCR was basically performed as described in U.S. Pat. No. 7,381,818 with the following modifications 35-45 cycles of three step PCR (95° C. for 30 s, 56° C. for 30 s and 76° C. for 30 s) after 2 min at 50° C. and 2 min at 95° C. were used. The reactions contained 0.25 µM MB-Fl-ODN-Q or non-MB probe, 100 nM primer complementary to the same strand as the probe, 1 µM opposite strand primer, 125 µM dATP, 125 µM dCTP, 125 µM TTP, 250 µM dUTP, 0.25 U JumpStart DNA polymerase (Sigma), 0.125U of AmpErase Uracil N-glycosylase (Applied Biosystems) in 1×PCR buffer (20 mM Tris-HCl pH 8.7, 40 mM NaCl, 5 mM $MgCl_2$) in a 10 µL reaction. The increase in fluorescent signal was recorded during the annealing step of the reaction.

Droplet Digital PCR Amplification ddPCR amplification was performed as described by Pinheiro et al., Anal Chem. 2012 January 17; 84(2): 1003-1011, the content of which is incorporated herein by reference.

Example 1

This example demonstrates the hybridization performance at room temperature (20° C. to 25° C., or ~22° C.) of a 10-mer MGB oligonucleotide compared to a non-MGB oligonucleotide demonstrating a) the improved background and b) the improved ability of the MGB oligonucleotide to discriminate the A and C alleles. The sequences of the probes specific for two short synthetic targets are shown in Table 1. Probe concentrations used were 600 nM and target concentrations 600 nM and hybridizations were performed in PCR buffer.

TABLE 1

Probe and synthetic target sequences for A- and C-alleles with Tms. T* is Super T, Q is the Eclipse Dark Quencher and FAM and AP 525 (U.S. Pat. No. 7,671,218) are fluorescent dyes. Alleles are shown in bold.

| Seq ID No | Type | Sequence (Oligo) | Tm °C. |
|---|---|---|---|
| 1 | MGB-AP525-Oligo-Q | TTATTTCTGC | 50.1 |
| 2 | MGB-FAM-Oligo-Q | TTATT*TATGC | 49.5 |
| 3 | AP525-Oligo-Q | TTATTTCTGC | 20.57 |
| 4 | FAM-Oligo-Q | TTATT*TATGC | 23.0 |
| 5 | Allele G synthetic target | CTGCAAATAGC AGAAATAAAAG AAA | |
| 6 | Allele T synthetic target | CTGCAAATAGC ATAAATAAAAG AAA | |

Figure 2:
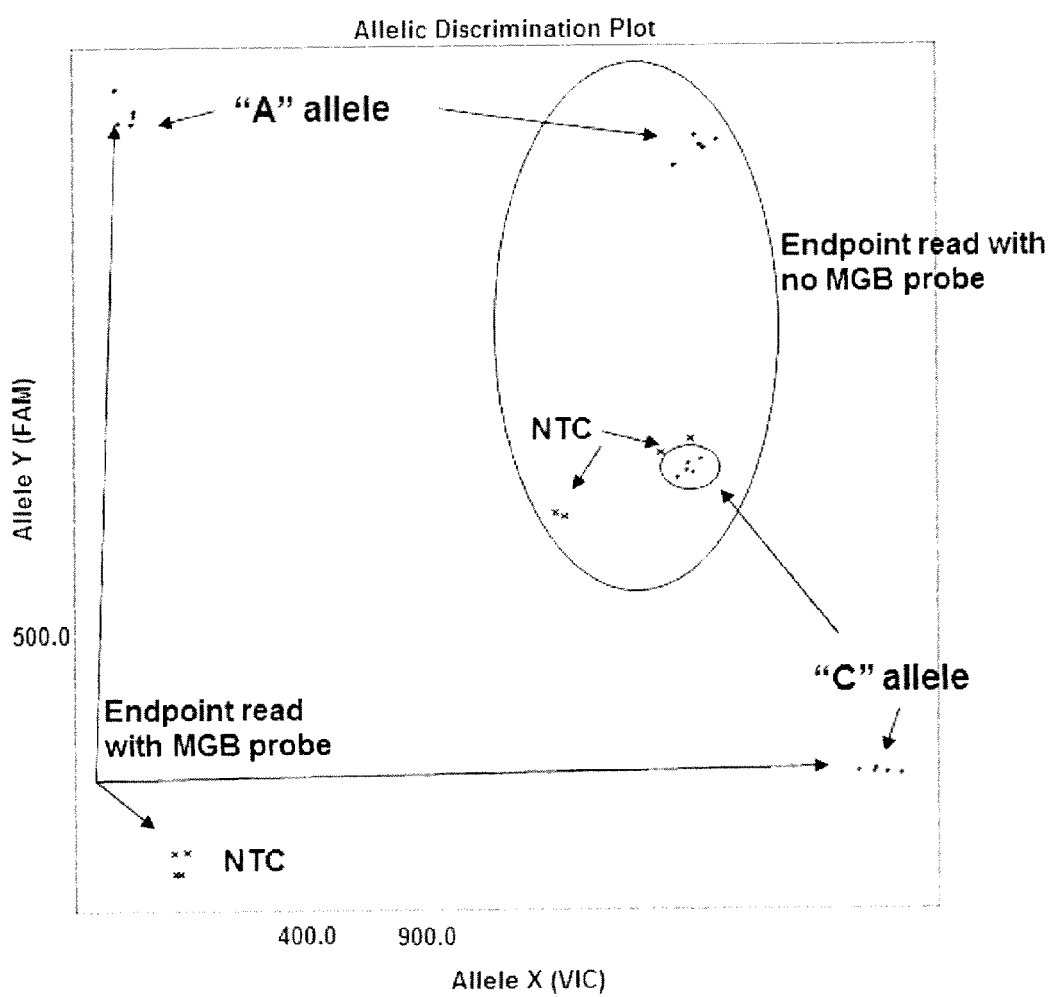
FIG. 2 shows a fluorescence scatter plot of 10-mer MGB-Fl-oligo-Q probes (Seq ID Nos. 1 and 2) and a 10-mer non-MGB probe (Seq ID Nos. 3 and 4), hybridized to synthetic targets containing "A" and a "C" alleles (Seq ID Nos. 5 and 6)

The raw melt fluorescent curves are shown in FIG. 1 for the FAM and Vic channels for both the 10-mer MGB probes (Seq. ID. Nos 1 and 2) and the 10-mer No-MGB probes (Seq. ID. Nos 3 and 4) when hybridized to synthetic targets (Seq. ID. Nos. 5 & 6). The raw melt fluorescent curves showed substantially higher background fluorescence for the no-MGB probes than the MGB probes. This was confirmed when a scatter plot was generated with replicate samples containing either "A" allele, "C" allele or no template control (NTC) using both the MGB probes and the no-MGB probes in FIG. 2. The high background with the non-MGB probes is reflected by the observation that the NTC and "C"-allele values are clumped closely together; in contrast the low background values of the MGB probes for the "C" allele values are locate a substantial distance from the NTC values.

Example 2

This example compares the hybridization performance at room temperature (~22° C.) of a 16/17-mer, 11-mer and 10-mer MGB MGB-Fl-oligo-Q probes, demonstrating the improved ability of the shorter MGB oligonucleotide to discriminate the A and C alleles. The sequences of the probes specific for two short synthetic targets are shown in Table 2. The concentrations used for 10-mer and 11-mer probes was 600 nM and for the 16/17-mers were 200 nM to compensate for the quenching that occurs in shorter MGB-Fl-oligo-Q probes. It is known that signal and background of a 10-mer MGB-Fl-oligo-Q probe is about half that of a 16-mer probe (Lukhtanov et al, Nucl. Acids Res., 35:e30 (2007)) due to closer distance between fluorophore and quencher. The target concentrations were equivalent to probe concentrations and hybridizations were performed in PCR buffer.

TABLE 2

MGB-Fl-oligo-Q Probe and synthetic target sequences for A- and C-alleles with Tms and ΔTms. T* is Super T, Q is the Eclipse Dark Quencher and FAM and AP 525 (U.S. Pat. No. 7,671,218) are fluorescent dyes.

| Seq ID No | Type | Sequence (Oligo) | Tm °C. | ΔTm °C. |
|---|---|---|---|---|
| 1 | MGB-AP525-Oligo-Q | TTATTTCTGC (10-mer) | 50.6 | 18.0 |
| 2 | MGB-FAM-Oligo-Q | TTATT*TATGC (10-mer) | 49.5 | 9.5 |
| 7 | MGB-AP525-Oligo-Q | TTATTTCTGCT (11-mer) | 54.4 | 18.2 |
| 8 | MGB-FAM-Oligo-Q | TTATT*TATGCT* (11-mer) | 54.3 | 8.1 |
| 9 | MGB-AP525-Oligo-Q | TTATTTCTGCTATTTG (16-mer) | 64.1 | 14.1 |
| 10 | MGB-FAM-Oligo-Q | TTTATT*TATGCTATT*T*G (17-mer) | 64.0 | 4.2 |
| 5 | Allele G synthetic target | CTGCAAATAGC AGAAATAAAAG AAA | | |
| 6 | Allele T synthetic target | CTGCAAATAGC ATAAATAAAAG AAA | | |

Figure 3:
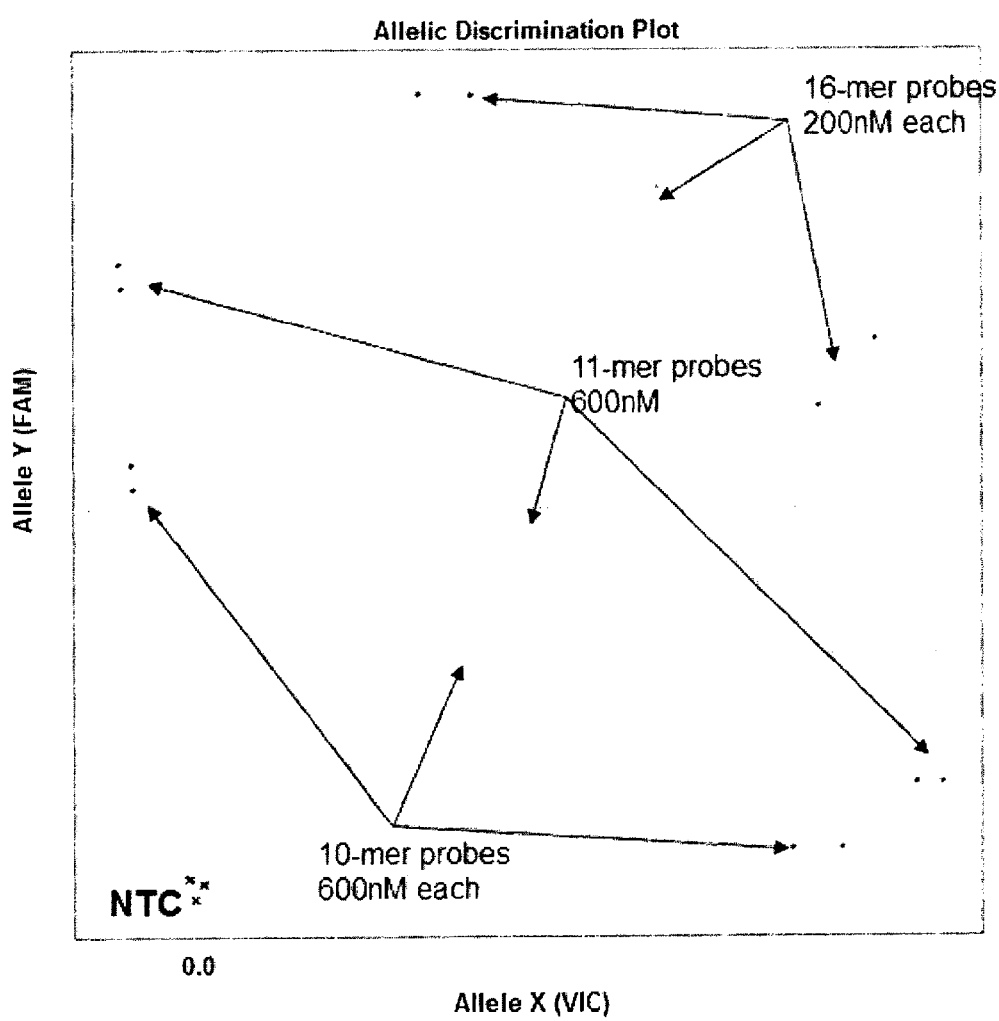
FIG. 3 shows a fluorescence scatter plot of 10-mer (Seq ID Nos. 1 and 2), 11-mer (Seq ID Nos. 7 and 8) and 16/17-mer MGB-Fl-oligo-Q probes (Seq ID Nos. 9 and 10), hybridized to synthetic targets containing "A" and a "C" alleles (Seq ID Nos. 5 and 6)

As shown in the Table 2, ability to discriminate the A:G mismatch as measured by ΔTm increases from 4.2° C. for the 17-mer (Seq.ID No 10) to 9.5° C. for the 10-mer (Seq. ID No 2). While the ΔTm increases from 14.1° C. for the 10-mer (Seq.ID No 9) to 17.3° C. for the 10-mer (Seq. ID No 1) for the C:T mismatch. This was confirmed when a scatter plot was generated with replicate samples containing either "A" allele, "C" allele or no template control (NTC) using the different MGB probes (Table 2) in FIG. 3.

Surprisingly, the shorter MGB-Fl-oligo-Q probes (10-mer or 11-mer) show substantially better discrimination compared to the 16/17-mer probes as reflected in the spacing of the "C" and "A" alleles values in the Scatter Plot.

Example 3

This example compares the ability of 30-mer TaqMank, 16/17-mer Pleiades and 10-mer Pleiades probes to discriminate allele rs 121912462 in the APC gene at room temperature of a digitally amplified genomic target. Target was amplified and detected as described (Pinheiro et al., Anal Chem. 2012 January 17: 84(2): 1003-1011) with the forward and reverse primer concentrations at 1000 nM and 250 nM respectively, and the probe concentration at 600 nM. The sequences of the probes specific for allele rs121912462 target are shown in Table 3.

TABLE 3

Primers and MGB-Fl-oligo-Q Probes specific for rs 121912462 in the APC gene with corresponding Tms.

| Seq ID No | Type | Sequence (Oligo) | Tm ° C. |
|---|---|---|---|
| 1 | MGB-AP525-Oligo-Q | TTATTTCTGC (10-mer) | 50.6 |
| 2 | MGB-FAM-Oligo-Q | TTATT*TATGC (10-mer) | 49.5 |
| 9 | MGB-AP525-Oligo-Q | TTATTTCTGCTATTTG (16-mer) | 64.1 |
| 10 | MGB-FAM-Oligo-Q | TTTATT*TATGCTATT*T*G (17-mer) | 64.0 |
| 11 | Hex-Oligo-Q | ACCCTGCAAATAGCAGAAAT AAAAGAAAAG | |
| 12 | FAM-Oligo-Q | ACCCTGCAAATAGCATAAAT AAAAGAAAAG | |
| 13 | Forward primer | GACACAGGAAGCAGATTCTG CTAATACC | |
| 14 | Reverse primer | CACAGGATCTTCAGCTGACC TAGTTC | |

Figure 4:
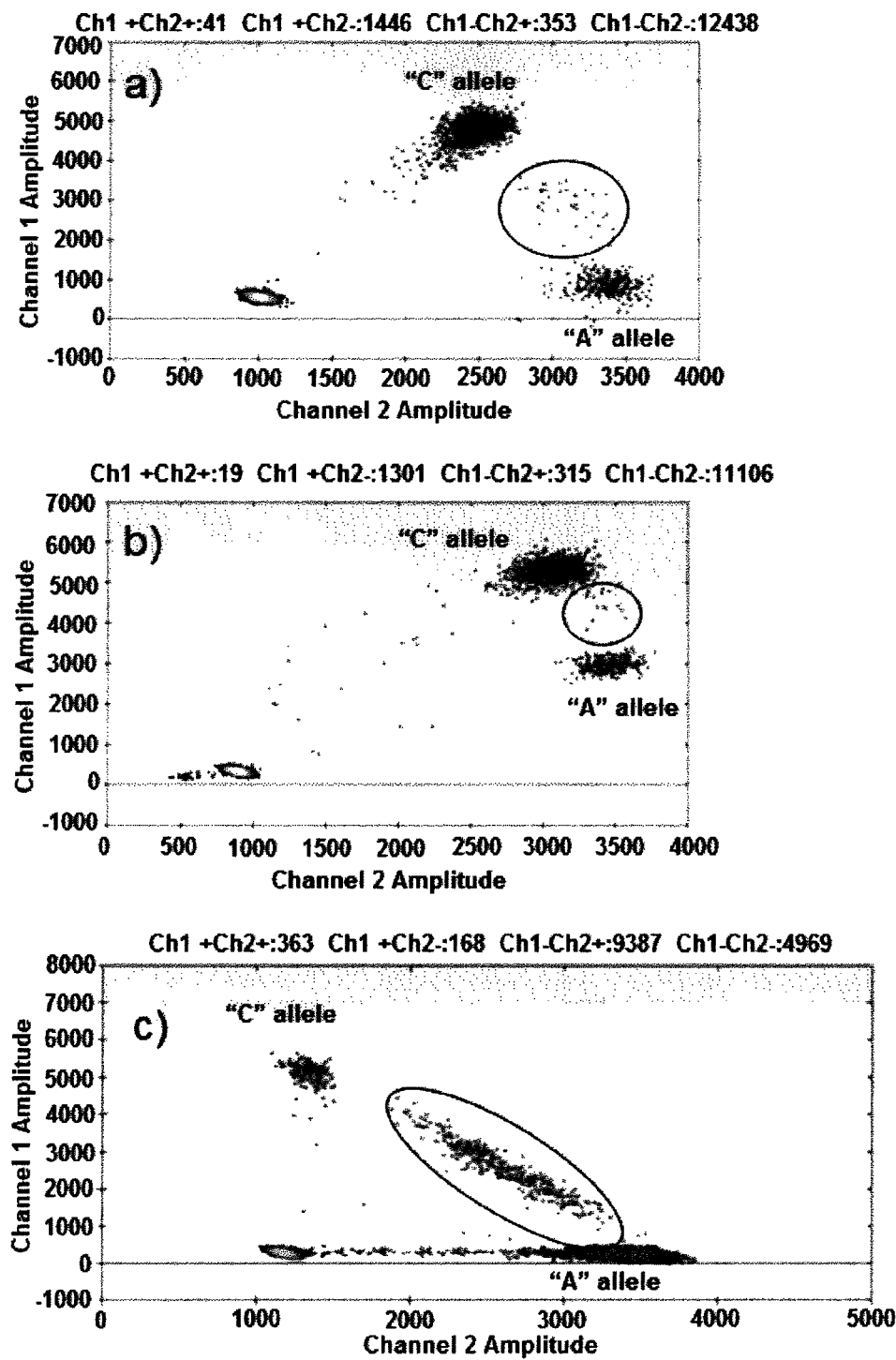
FIGS. 4a), 4b) and 4c) show, respectively, the scatter plots of fluorescent detection with 30-mer TaqMan dual labeled probes (Seq ID Nos. 11 and 12), 16/17-mer MGB-Fl-oligo-Q probes (Seq ID Nos. 9 and 10) and 10-mer MGB-Fl-oligo-Q probe (Seq ID Nos. 1 and 2) of ddPCR amplified allele rs 121912462 in the APC gene at room temperature.

The Scatter Plots of fluorescent detection with the 30-mer TaqMan dual labeled probes (Seq ID No. 11 and 12), 16/17-mer Pleiades probes (Seq ID No. 9 and 10) and 10-mer Pleiades probe (Seq ID No. 1 and 2) of ddPCR amplified allele rs 121912462 in the APC gene at room temperature is shown respectively in FIGS. 4a), 4b) and 4c) for human genomic DNA sample. As shown in FIGS. 4a) and 4b) heterozygous samples (shown in the circle) are bunched closely together with the "A" and "C" alleles. In contrast, the heterozygous samples and especially the "C" allele in FIG. 4c), are well separated, allowing a more accurate detection of low abundance alleles.

Example 4

This example demonstrates similar performance of 10-mer MGB-Fl-oligo-Q probes to discriminate alleles of the rs121913529 SNP in the KRAS gene at room temperature of a digitally amplified human genomic DNA. Target was amplified and detected as described in Example 3. The Scatter Plot with the 10-mer MGB-Fl-oligo-Q probes listed in Table 4 (Seq ID Nos 13 and 14) is shown FIG. 5.

TABLE 4

Primers and MGB Pleiades Probes specific for rs121913529 in the KRAS gene with corresponding Tms.

| Seq ID No | Type | Sequence (Oligo) | Tm ° C. |
|---|---|---|---|
| 15 | MGB-AP525-Oligo-Q | G*AGCTGGTGG | 47 |
| 16 | MGB-FAM-Oligo-Q | G*AGCTGATGG | 49 |
| 17 | Forward primer | CCTGCTGAAAA TGACTGAATAT AAACTTGT | |
| 18 | Reverse primer | GCTGTATCGTC AAGGCACTC | |

Figure 5:
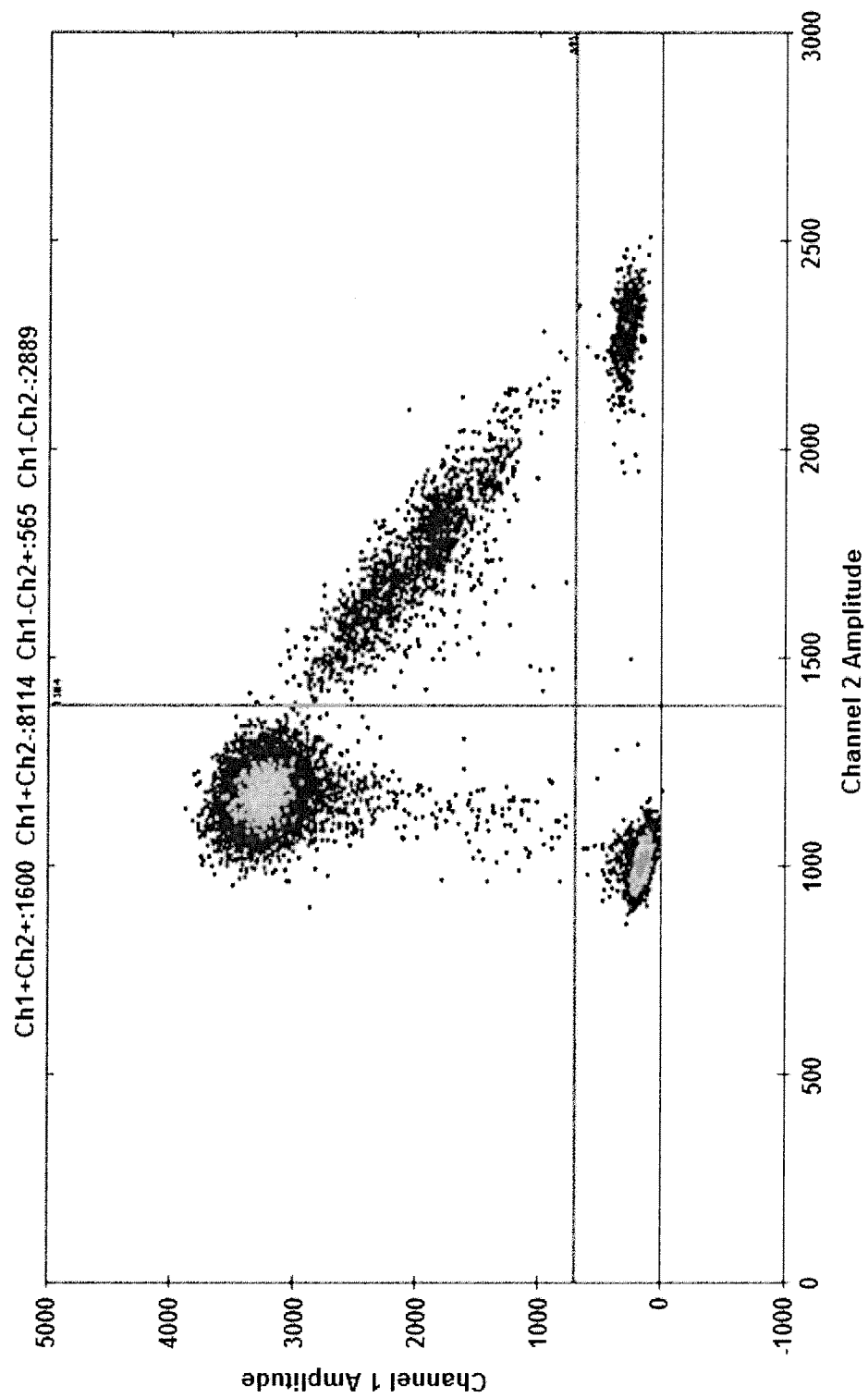
FIG. 5 shows the scatter plots of fluorescent detection with 10-mer MGB-Fl-oligo-Q probes (Seq ID Nos. 15 and 16) of ddPCR amplified allele rs 121913529 in the KRAS gene at room temperature.

As shown in FIG. 5, 10-mer Pleiades probes discriminate well between "C" and "T" alleles of the amplified allele rs 121913529 in the KRAS gene with defined spacing between, the heterozygous, G" and "A" alleles of the amplified KRAS gene.

REFERENCES CITED

The following references, to the extent that they provide exemplary procedural or other details supplementary to those set forth herein, are specifically incorporated herein by reference.

United States Patent Documents

U.S. Pat. Nos. 6,440,706

6,440,706

7,381,818

7,759,126

Non-Patent Literature

Chang and Shih, *Methods Mol Med.* 103:137-41 (2005)

Hindson et al, *Anal. Chem.*, 83: 8604-8610 (2011)

Pinheiro et al., *Anal Chem.* 2012 January 17; 84(2): 1003-1011

Strain et al., *PLoS One.* 2013; 8(4):e55943

Tsui et al, *Clin Chem.* 56(1):73-81 (2010)

Vogelstein and Kinzler, *Proc. Natl. Acad. Sci. USA,* 96: 9236-9241 (1999)

The invention claimed is:

1. A method for discriminating mismatch in a target DNA sample, comprising:
contacting the target DNA sample with a first minor groove binder oligonucleotide probe and a second minor groove binder oligonucleotide probe;
detecting fluorescent signals from the first and second minor groove binder oligonucleotide probes;
wherein the oligonucleotide portion of the first minor groove binder oligonucleotide probe has a first sequence that is complementary to a region of the target DNA sample, wherein the oligonucleotide portion of the second minor groove binder oligonucleotide probe has a second sequence that differs from the first sequence by one base, and wherein the target DNA sample is digitally amplified DNA resulting from a ddPCR reaction;
wherein the first and second minor groove binder oligonucleotide probes have the formula:

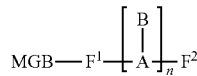

wherein MGB M is a minor groove binder;
wherein $F^1 = F^2$ is a fluorophore or a quencher, wherein $F^1$ and $F^2$ cannot both be quenchers or both be fluorophores, and wherein the fluorophore of the first minor groove binder oligonucleotide probe differs from the fluorophore of the second minor groove binder oligonucleotide probe;
wherein $[A-B]_n$ represents the oligonucleotide portion of the first and second minor groove binder oligonucleotide probes, and wherein the oligonucleotide portion has n units, wherein n is an integer of from 9 to 11;
wherein each A independently represents a sugar phosphate backbone, a modified sugar phosphate backbone, a locked nucleic acid backbone, or a peptidic backbone or a variant thereof; and
wherein each B independently represents a nucleic acid base, a modified base, a base analog, or a universal base;
generating a scatter plot of the fluorescent signals of the first and second minor groove binder oligonucleotide probes; and
using the scatter plot to discriminate mismatches in the target DNA sample.

2. The method of claim 1, wherein the detecting is performed at approximately 20° C. to 25° C.

3. The method of claim 1, wherein the quencher has absorption spectra between about 400 to 800 nm and the fluorophore has emission between about 400 to 800 nm.

4. The method of claim 1, wherein the minor groove binder oligonucleotide probe comprises at least one B independently selected from a nucleic acid base, a modified base or a base analog, or a universal base.

5. The method of claim 4, wherein the modified base is 6-amino-1H-pyrazolo[3,4-d]pyrimidin-4(5H)-one, 4-(4,6-Diamino-1H-pyrazolo[3,4-d]pyrimidin-3-yl)-but-3-yn-1-ol, 5-(4-hydroxy-but-1-ynyl)-1H-pyrimidine-2,4-dione, or 3-alkynyl-1H-pyrazolo[3,4-d]pyrimidin-4(5H)-one.

6. The method of claim 1, wherein $F^1$ is a fluorophore and $F^2$ is a quencher.

7. The method of claim 1, wherein $F^2$ is a fluorophore and $F^1$ is a quencher.

8. The method of claim 1, wherein the MGB is attached at the 3'-end of the oligonucleotide.

9. A first and second minor groove binder oligonucleotide probe having the formula:

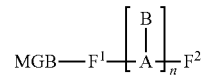

wherein MGB M is a minor groove binder;
wherein $F^1 = F^2$ is a fluorophore or a quencher, wherein $F^1$ and $F^2$ cannot both be quenchers or both be fluorophores, and wherein the fluorophore of the first minor groove binder oligonucleotide probe differs from the fluorophore of the second minor groove binder oligonucleotide probe;
wherein $[A-B]_n$ represents an oligonucleotide portion of the first and second minor groove binder oligonucleotide probes, and wherein the oligonucleotide portion has n units, wherein n is an integer of from 9 to 11;
wherein each A independently represents a sugar phosphate backbone, a modified sugar phosphate backbone, a locked nucleic acid backbone, or a peptidic backbone or a variant thereof;
wherein each B independently represents a nucleic acid base, a modified base, a base analog, or a universal base;
wherein the oligonucleotide portion of the first minor groove binder oligonucleotide probe has a first sequence that is complementary to a target DNA sample, wherein the oligonucleotide portion of the second minor groove binder oligonucleotide probe has a second sequence that differs from the first sequence by one base, and the target DNA sample is digitally amplified DNA resulting from a ddPCR reaction.

10. The first and second minor groove binder oligonucleotide probe of claim 9, wherein the quencher has absorption spectra between about 400 to 800 nm and the fluorophore has emission between about 400 to 800 nm.

11. The first and second minor groove binder oligonucleotide probe of claim 9, wherein the minor groove binder oligonucleotide probe comprises at least one B independently selected from a nucleic acid base, a modified base or a base analog, or a universal base.

12. The first and second minor groove binder oligonucleotide probe of claim 11, wherein the modified base is 6-amino-1H-pyrazolo[3,4-d]pyrimidin-4(5H)-one, 4-(4,6-Diamino-1H-pyrazolo[3,4-d]pyrimidin-3-yl)-but-3-yn-1-ol, 5-(4-hydroxy-but-1-ynyl)-1H-pyrimidine-2,4-dione, or 3-alkynyl-1H-pyrazolo[3,4-d]pyrimidin-4(5H)-one.

13. The first and second minor groove binder oligonucleotide probe of claim 9, wherein $F^1$ is a fluorophore and $F^2$ is a quencher.

14. The first and second minor groove binder oligonucleotide probe of claim 9, wherein $F^2$ is a fluorophore and $F^1$ is a quencher.

15. The minor groove binder oligonucleotide probe of claim 9, wherein the MGB is attached at the 3'-end of the oligonucleotide.

* * * * *